(12) United States Patent
Mickley et al.

(10) Patent No.: US 6,264,630 B1
(45) Date of Patent: Jul. 24, 2001

(54) BALLOON CATHETER HAVING AN OSCILLATING TIP CONFIGURATION

(75) Inventors: Timothy J. Mickley, Elk River; Chad G. Harris, Big Lake, both of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/219,802

(22) Filed: Dec. 23, 1998

(51) Int. Cl.$^7$ .................. A61M 29/00; A61M 25/00; A61M 25/01

(52) U.S. Cl. .............. 604/96.01; 604/523; 604/524; 604/528

(58) Field of Search ................. 604/96–98, 523, 604/524, 528, 912, 915, 921, 103; 606/192–194

(56) References Cited

U.S. PATENT DOCUMENTS

| Re. 33,166 | 2/1990 | Samson ........................... 606/194 |
|---|---|---|
| 3,911,927 | 10/1975 | Rich et al. ....................... 128/349 R |
| 4,085,185 | 4/1978 | Adair .................................. 264/248 |
| 4,195,637 | 4/1980 | Grüntzig et al. ................... 128/348 |
| 4,249,536 | 2/1981 | Vega ................................. 128/349 B |
| 4,251,305 | 2/1981 | Becker et al. ......................... 156/86 |
| 4,307,722 | 12/1981 | Evans ................................... 128/344 |
| 4,323,071 | 4/1982 | Simpson et al. ..................... 128/343 |
| 4,385,635 | 5/1983 | Ruiz ..................................... 128/658 |
| 4,413,989 | 11/1983 | Schjeldahl et al. ................... 604/96 |
| 4,425,919 | 1/1984 | Alston, Jr. et al. ................... 128/658 |
| 4,531,512 | 7/1985 | Wolvek et al. ...................... 128/1 D |

(List continued on next page.)

FOREIGN PATENT DOCUMENTS

| 0 171 884 A1 | 2/1986 | (EP) . |
|---|---|---|
| 0 237 564 B1 | 9/1987 | (EP) . |
| 0 448 886 A1 | 10/1991 | (EP) . |
| 0 452 595 A1 | 10/1991 | (EP) . |
| 0 452 901 B1 | 10/1991 | (EP) . |
| 0 594 201 A2 | 4/1994 | (EP) . |
| 0 688 576 A1 | 12/1995 | (EP) . |
| 0 689 852 A1 | 1/1996 | (EP) . |
| 0 787 504 A2 | 8/1997 | (EP) . |
| 8-266636 | 10/1996 | (JP) . |
| WO 93/17750 | 9/1993 | (WO) . |
| WO 94/01160 | 1/1994 | (WO) . |
| WO 95/01752 | 1/1995 | (WO) . |

OTHER PUBLICATIONS

*Plastics Digest*, Edition 15, vol. 2, 1994, p. 2–314.
Kohan, *Nylon Plastics Handbook*, Hanser/Gardner Publications, Inc., Cincinnati, Ohio, Copyright 1995, pp. 378–387.

Primary Examiner—Richard K. Seidel
Assistant Examiner—Michael J Hayes
(74) Attorney, Agent, or Firm—Crompton, Seager & Tufte, LLC (57) ABSTRACT

A catheter is disclosed which includes an over-the-wire type balloon catheter, with a guide wire, wherein the catheter incorporates an axially movable inner tubular member which extends proximally through a proximal manifold lumen. The inner tubular member extends distally beyond the distal end of the outer tubular member with the balloon member distal waist affixed to the inner tubular member proximate the distal end. The catheter incorporates axial tension members which function to transmit force to the distal tip when the movable inner tubular member is oscillated axially. The axial tension members are preferably a plurality of wires, each having a proximal end affixed to the outside diameter of the inner tubular member proximate the manifold, and each having a distal end affixed to the outside diameter of the inner tubular member a substantial distance distal of the manifold. When the inner tubular member is pulled proximally, energy is stored in the catheter, which when the inner is released, forces the distal tip forward with added force from the distal point of attachment of the axial tension members. An actuator and a valve assembly are preferably included.

23 Claims, 3 Drawing Sheets

U.S. PATENT DOCUMENTS

| | | | |
|---|---|---|---|
| 4,531,943 | 7/1985 | Van Tassel et al. | 604/280 |
| 4,540,404 | 9/1985 | Wolvek | 604/96 |
| 4,551,292 | 11/1985 | Fletcher et al. | 264/139 |
| 4,588,399 | 5/1986 | Nebergall et al. | 604/280 |
| 4,596,563 | 6/1986 | Pande | 604/264 |
| 4,636,272 | 1/1987 | Riggs | 156/158 |
| 4,636,346 | 1/1987 | Gold et al. | 264/139 |
| 4,650,467 | 3/1987 | Bonello et al. | 604/95 |
| 4,676,229 | 6/1987 | Krasmicki et al. | 128/4 |
| 4,686,982 | 8/1987 | Nash | 128/305 |
| 4,706,670 | 11/1987 | Andersen et al. | 128/344 |
| 4,739,768 | 4/1988 | Engelson | 128/658 |
| 4,748,982 | 6/1988 | Horzewski et al. | 128/344 |
| 4,753,765 | 6/1988 | Pande | 264/149 |
| 4,758,221 | 7/1988 | Jureidini | 604/95 |
| 4,759,748 | 7/1988 | Reed | 604/95 |
| 4,764,324 | 8/1988 | Burnham | 264/103 |
| 4,782,834 | 11/1988 | Maguire et al. | 128/344 |
| 4,808,164 | 2/1989 | Hess | 604/95 |
| 4,817,613 | 4/1989 | Jaraczewski et al. | 128/658 |
| 4,819,751 | 4/1989 | Shimada et al. | 128/344 |
| 4,820,349 | 4/1989 | Saab | 128/344 |
| 4,848,342 | 7/1989 | Kaltenbach | 128/341 |
| 4,854,325 | 8/1989 | Stevens | 128/657 |
| 4,863,442 | 9/1989 | DeMello et al. | 604/282 |
| 4,870,953 | 10/1989 | DonMicheal et al. | 128/24 A |
| 4,884,573 | 12/1989 | Wijay et al. | 128/344 |
| 4,886,506 | 12/1989 | Lovgren et al. | 604/280 |
| 4,898,896 | 2/1990 | Maj et al. | 528/323 |
| 4,906,244 | 3/1990 | Pinchuk et al. | 606/194 |
| 4,921,483 | 5/1990 | Wijay et al. | 604/96 |
| 4,943,278 | 7/1990 | Euteneuer et al. | 604/96 |
| 4,955,377 | 9/1990 | Lennox et al. | 128/401 |
| 4,960,410 | 10/1990 | Pinchuk | 604/96 |
| 4,964,409 | 10/1990 | Tremulis | 128/657 |
| 4,964,853 | 10/1990 | Sugiyama et al. | 604/96 |
| 4,976,720 | 12/1990 | Machold et al. | 606/194 |
| 4,994,018 | 2/1991 | Saper | 600/18 |
| 5,002,559 | 3/1991 | Tower | 606/194 |
| 5,047,045 | 9/1991 | Arney et al. | 606/194 |
| 5,050,606 | 9/1991 | Tremulis | 128/637 |
| 5,078,702 | 1/1992 | Pomeranz | 604/280 |
| 5,078,727 | 1/1992 | Hannam et al. | 604/194 |
| 5,093,546 | 3/1992 | Matsumiya et al. | 219/10.41 |
| 5,100,381 | 3/1992 | Burns | 604/96 |
| 5,100,426 | 3/1992 | Nixon | 606/170 |
| 5,116,350 | 5/1992 | Stevens | 606/159 |
| 5,120,308 | 6/1992 | Hess | 604/95 |
| 5,122,125 | 6/1992 | Deuss | 604/282 |
| 5,139,496 | 8/1992 | Hed | 606/23 |
| 5,143,093 | 9/1992 | Sahota | 128/898 |
| 5,147,377 | 9/1992 | Sahota | 606/194 |
| 5,154,725 | 10/1992 | Leopold | 606/194 |
| 5,156,594 | 10/1992 | Keith | 604/96 |
| 5,156,612 | 10/1992 | Pinchuk et al. | 606/194 |
| 5,158,548 | 10/1992 | Lau et al. | 604/96 |
| 5,159,937 | 11/1992 | Tremulis | 128/772 |
| 5,163,421 | 11/1992 | Bernstein et al. | 128/24.1 |
| 5,171,230 | 12/1992 | Eland et al. | 604/250 |
| 5,176,637 | 1/1993 | Sagae | 604/96 |
| 5,180,585 | 1/1993 | Jacobson et al. | 424/405 |
| 5,195,972 | 3/1993 | Inoue | 604/103 |
| 5,209,728 | 5/1993 | Kraus et al. | 604/96 |
| 5,213,574 | 5/1993 | Tucker | 604/93 |
| 5,221,270 | 6/1993 | Parker | 604/282 |
| 5,226,888 | 7/1993 | Arney | 604/96 |
| 5,234,416 | 8/1993 | Macaulay et al. | 604/282 |
| 5,240,537 | 8/1993 | Bodicky | 156/244.13 |
| 5,243,997 | 9/1993 | Uflacker et al. | 128/772 |
| 5,254,091 | 10/1993 | Aliahmad et al. | 604/96 |
| 5,256,144 | 10/1993 | Kraus et al. | 604/96 |
| 5,258,160 | 11/1993 | Utsumi et al. | 264/558 |
| 5,259,839 | 11/1993 | Burns | 604/99 |
| 5,269,297 | 12/1993 | Weng et al. | 128/24 AA |
| 5,270,086 | 12/1993 | Hamlin | 428/35.2 |
| 5,279,561 | 1/1994 | Roucher et al. | 604/96 |
| 5,279,562 | 1/1994 | Sirhan et al. | 604/96 |
| 5,304,134 | 4/1994 | Kraus et al. | 604/96 |
| 5,304,198 | 4/1994 | Samson | 606/194 |
| 5,316,706 | 5/1994 | Muni et al. | 264/25 |
| 5,318,032 | 6/1994 | Lonsbury et al. | 128/658 |
| 5,318,527 | 6/1994 | Hyde et al. | 604/95 |
| 5,318,532 | 6/1994 | Frassica | 604/96 |
| 5,324,259 | 6/1994 | Taylor et al. | 604/96 |
| 5,324,263 | 6/1994 | Kraus et al. | 604/96 |
| 5,328,468 | 7/1994 | Kaneko et al. | 604/96 |
| 5,334,148 | 8/1994 | Martin | 604/96 |
| 5,334,168 | 8/1994 | Hemmer | 604/281 |
| 5,335,410 | 8/1994 | Burnham | 29/452 |
| 5,342,386 | 8/1994 | Trotta | 606/194 |
| 5,344,395 * | 9/1994 | Whalen et al. | 604/22 |
| 5,344,400 | 9/1994 | Kaneko et al. | 604/96 |
| 5,346,505 | 9/1994 | Leopold | 606/194 |
| 5,364,357 | 11/1994 | Aase | 604/96 |
| 5,370,615 | 12/1994 | Johnson | 604/96 |
| 5,370,655 | 12/1994 | Burns | 606/194 |
| 5,380,273 | 1/1995 | Dubrul et al. | 604/22 |
| 5,383,852 | 1/1995 | Stevens-Wright | 604/95 |
| 5,387,193 | 2/1995 | Miraki | 604/96 |
| 5,389,087 | 2/1995 | Miraki | 604/247 |
| 5,397,306 | 3/1995 | Nobuyoshi et al. | 604/96 |
| 5,399,164 | 3/1995 | Snoke et al. | 604/95 |
| 5,403,292 | 4/1995 | Ju | 604/282 |
| 5,405,338 | 4/1995 | Kranys | 604/282 |
| 5,411,477 | 5/1995 | Saab | 604/96 |
| 5,423,754 | 6/1995 | Cornelius et al. | 604/103 |
| 5,425,709 | 6/1995 | Gambale | 604/96 |
| 5,425,712 | 6/1995 | Goodin | 604/96 |
| 5,449,369 | 9/1995 | Imran | 606/159 |
| 5,454,795 | 10/1995 | Samson | 604/282 |
| 5,458,613 | 10/1995 | Gharibadeh et al. | 606/194 |
| 5,470,322 | 11/1995 | Horzewski et al. | 604/280 |
| 5,480,383 | 1/1996 | Bagaoisan | 604/96 |
| 5,496,271 | 3/1996 | Burton et al. | 604/54 |
| 5,496,294 | 3/1996 | Hergenrother et al. | 604/282 |
| 5,503,263 | 4/1996 | Watanabe | 198/442 |
| 5,509,910 | 4/1996 | Lunn | 604/282 |
| 5,524,635 | 6/1996 | Uflacker et al. | 128/772 |
| 5,531,715 | 7/1996 | Engelson et al. | 604/265 |
| 5,538,513 | 7/1996 | Okajima | 604/282 |
| 5,540,236 | 7/1996 | Ginn | 128/772 |
| 5,542,924 | 8/1996 | Snoke et al. | 604/95 |
| 5,542,937 | 8/1996 | Chee et al. | 604/280 |
| 5,549,119 | 8/1996 | Solar | 128/772 |
| 5,549,552 | 8/1996 | Peters et al. | 604/96 |
| 5,549,556 | 8/1996 | Ndondo-Lay et al. | 604/102 |
| 5,554,121 | 9/1996 | Ainsworth et al. | 604/96 |
| 5,554,139 | 9/1996 | Okajima | 604/282 |
| 5,569,179 | 10/1996 | Adrian | 604/22 |
| 5,569,218 | 10/1996 | Berg | 604/282 |
| 5,605,543 | 2/1997 | Swanson | 604/96 |
| 5,609,606 | 3/1997 | O'Boyle | 606/194 |
| 5,611,807 | 3/1997 | O'Boyle | 606/169 |
| 5,626,593 | 5/1997 | Imran | 606/159 |
| 5,643,209 | 7/1997 | Fugoso et al. | 604/96 |
| 5,645,528 | 7/1997 | Thome | 604/96 |
| 5,716,373 | 2/1998 | Wolvek et al. | 606/194 |
| 5,725,513 | 3/1998 | Ju et al. | 604/280 |
| 5,728,063 | 3/1998 | Preissman et al. | 604/96 |
| B1 4,323,071 | 5/1990 | Simpson et al. | 128/343 |

* cited by examiner

BALLOON CATHETER HAVING AN OSCILLATING TIP CONFIGURATION

TECHNICAL FIELD

This invention relates to the field of intravascular medical devices used in combination with guide members. More specifically, the present invention relates to intravascular balloon dilatation catheters for use in combination with guide wires, wherein the catheter incorporates means for axially oscillating the inner tubular member in combination with axial tensioning members which transfer force during oscillation of the inner tube to the distal tip of the catheter for crossing tight obstructions and bends in vessel lumens.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guide wire, possibly in combination with other intravascular devices. A typical balloon catheter has an elongate shaft with a balloon attached proximate the distal end and a manifold attached proximate the proximal end. In use, the balloon catheter is advanced over the guide wire such that the balloon is positioned adjacent a restriction in a diseased vessel. The balloon is then inflated and the restriction in the vessel is opened.

There are two basic types of balloon catheters used in combination with a guide wire, namely, over-the-wire (OTW) catheters and single-operator-exchange (SOE) catheters. The construction and use of both standard OTW catheters and standard SOE catheters are well-known in the art. An example of an OTW catheter may be found in commonly-assigned U.S. Pat. No. 5,047,045 to Arney et al. An example of an SOE balloon catheter is disclosed in commonly-assigned U.S. Pat. No. 5,156,594 to Keith.

PTA and PTCA catheters are preferably designed to optimize pushability, trackability and crossability. Pushability is defined as the ability to transmit force from the proximal end of the catheter to the distal end of the catheter. Trackability is defined as the ability to navigate tortuous vasculature. Crossability is defined as the ability to navigate the balloon catheter across narrow restrictions or obstructions in the vasculature.

One type of OTW balloon catheter is a coaxial OTW balloon catheter. A coaxial OTW catheter typically includes two separate tubes, namely an inner tube and a coaxially disposed outer tube. The inner tube defines a guide wire lumen and an annular inflation lumen is defined between the inner tube and the coaxially disposed outer tube. In a standard OTW coaxial catheter, the outer tube has a proximal end which is fixed to a manifold with the lumen of the outer tube in fluid communication with a side port in the manifold for injection of inflation fluid. The outer tube extends distally to the proximal waist of an inflatable balloon, with the proximal waist of the balloon secured to the distal portion of the outer tubular member. The lumen of the outer tubular member is in fluid communication with the internal volume of the balloon. The inner tubular member also includes a proximal end which terminates in the manifold, however, the inner tubular member terminates at a point proximal to the termination of the outer tubular member with the lumen of the inner tube extending straight through the manifold to a port which is axially aligned with the lumen so that a guide wire may be extended therethrough. The side port of the manifold for inflation is thus only in fluid communication with the annular space formed between the tubes. The inner tubular member extends distally to a point beyond the distal termination of the outer tubular member with the inflatable balloon extending from proximate the distal end of the outer tubular member to a point proximate the distal end of the inner tubular member onto which it is adhered. The manifold attachment of the inner and outer tubular members secures these tubular members relative to each other.

Prior art coaxial OTW-type balloon catheters have attempted to maximize pushability by incorporating a stainless steel outer tube on the proximal shaft portion (also referred to as a hypotube) and a polymeric distal shaft portion. Hypotubing is, however, prone to kinking. Coaxial OTW-type balloon catheters can also incorporate a polymer shaft or a reinforced polymer shaft as a proximal shaft portion (e.g. composite) with recognized loss of pushability as a compromise between maximizing pushability and minimizing the probability of kinking in the proximal shaft portion.

The trackability of a particular catheter design is analyzed in terms of the trackability of the distal portion of the catheter, as this portion must track the guidewire through small tortuous vessels to reach the stenosed area to be treated. A more flexible distal portion has been found to improve trackability. Further, in transitioning from a stiff proximal segment or portion of the catheter shaft to a more flexible distal portion of the catheter shaft, it has been found that kinking readily occurs at the joint between the two shaft segments of differing flexibility. The increased flexibility of the distal section also makes this portion of the catheter less able to be pushed from the proximal end of the catheter.

Even with the prior art emphasis on improved pushability, trackability and crossability, it has still been found that there are many stenotic lesions or restrictions in blood vessels through which present OTW catheters cannot be passed. In some of these restricted vessel regions, it is possible to pass the guide wire distal portion through the restriction, yet it is found that the balloon angioplasty catheter itself cannot cross the restriction to place the balloon for expansion. This has also been found to be true when metallic stents, which are presently utilized for permanently holding a blockage open, are already within the blood vessel lumen through which a catheter must be tracked. The stent itself includes struts of wire having interstitial spaces between such struts into which the catheter distal tip can become lodged and caught. This can prevent further advancement through the stent lumen.

Many times the problems associated with crossing the placed stent or, in the alternative, crossing a tight vascular restriction present within the vessel, are compounded by the tortuous path that the lumen of the vessel follows at that point. In particular, it has been found to be difficult to pass the catheter through a highly restricted bend or through a stent which is placed within a bend in the vessel. There is, therefore, a need for a balloon dilatation catheter which incorporates features for improving the ability of the catheter to cross a tight vascular restriction or otherwise blocked region of the vessel through which a guide wire has already been placed. Further, there is a need for a balloon dilatation catheter having improved capability for passing through the lumen formed by a stent placed within the vessel, which would otherwise cause present distal tips on catheters to catch on or lodge against the stent struts.

SUMMARY OF THE INVENTION

The present invention may be described as a medical system including an over-the-wire type balloon catheter and a guide wire wherein the catheter inner tubular member is axially moveable, yet releasably securable in the axial direction relative to the outer tubular member and manifold. The catheter includes a means for axially oscillating the proximal end of the inner tubular member which works in combination with axial tensioning members extending over a portion of the length of the inner tubular member to transfer oscillating force to the catheter tip or distal end of the inner. The catheter preferably includes a polyethylene inner tube and an outer tube having a relatively stiff proximal outer section, a midshaft section of lesser stiffniess, and a tapering distal outer section of the least stiffness. Such an arrangement of progressively more flexible materials as the catheter proceeds distally provides an optimal level of pushability and trackability to navigate tortuous vasculature, yet the ability to axially oscillate the tip of the catheter via the inner tube further improves the catheter's ability to cross a narrow blockage through which a guide wire has been placed or to cross a placed stent, especially in a bend in the vessel lumen..

In a preferred embodiment, the inner tube defines a guide wire lumen and is coaxially disposed inside the outer tube to define an annular inflation lumen therebetween. An inflatable balloon has a distal end connected to the inner tube proximate the distal end of the inner tube, and a proximal end of the balloon is connected to the outer tube proximate the outer tube distal end. The guide wire has a maximum outside diameter which is less than the minimum inside diameter of the guide wire lumen such that the guide wire may be removed from or inserted into the guide wire lumen at either end of the catheter.

In preferred embodiments, a distal tip is formed at the distal end of the inner tube wherein a distal portion of the inner tube extends distally beyond the site where the distal waist of the balloon is bonded to the distal end of the inner tube. Within this bonding region, the distal end of the inner tube preferably tapers to a smaller outer diameter. In another embodiment, a tapering distal tip of lesser stiffness is heat welded to the distal end of the inner at an axial location under the balloon's distal waist. An OTW catheter incorporating these features is disclosed in commonly assigned co-pending application Ser. No. 08/950,864, filed Oct. 15, 1997, entitled "Over-the-Wire Catheter with Improved Trackability", the disclosure of which is incorporated herein by reference.

The present invention is directed to improving an OTW catheter by providing a way to oscillate the distal tip of the catheter in the axial direction to assist in crossing tight blockages, assist in navigating around the bend in a vessel lumen, or assist in passing through a placed stent within the vessel. However, simply oscillating the distal tip of the catheter could be accomplished with present designs simply by pulling the catheter back and forth in an axial direction over the guide wire. Although of some assistance in crossing a blockage, this type of oscillation has limitations as the pushing and pulling from the proximal end of the catheter provides limited force on the distal tip of the catheter. Much of the force is absorbed by the flexibility of the tubular members over the extensive length of the catheter when the catheter is pushed. An analogy to this problem would be pushing on a piece of rope which allows only limited force transfer from one end to the other prior to bending or buckling. One way to overcome such buckling problem is to place a hand around the tubular member closer to the distal end so that the distance between the point where forward force is applied and the distal end is smaller or shorter with the resultant reduction in potential for bending and buckling.

However, with an intravascular catheter, this is not possible since the vast majority of the catheter is inserted within the vessel lumen during use; it is only possible to act on the proximal portion of the catheter which extends outside of the body. The present invention overcomes this problem by incorporating a combination of features detailed below.

First, the catheter of the present invention includes an inner tubular member which is axially movable relative to the manifold and outer tubular member. As with a standard OTW catheter, the inner tubular member is bonded proximate its distal end to the distal waist of the balloon. However, the proximal end of the inner tubular member is extended through the manifold and out the proximal end thereof. The proximal end of the manifold includes means for releasably securing and/or sealing the inner tubular member as it passes through the proximal end. Thus, the inner tubular member may be oscillated in an axial direction as it slides within the manifold and within the outer tubular member. The means for securing and/or sealing the inner tubular member allows the inner tubular member to be fixed during balloon inflation and also prevents inflation fluid from leaking around the outside diameter of the inner tubular member during such balloon inflation.

In a preferred embodiment, the inner tubular member is relatively flexible; therefore, simply oscillating the inner tubular member axially is believed insufficient for transferring adequate force from the proximal end of the inner tubular member to the distal tip for crossing a tight blockage. To this end, a preferred embodiment of the present invention incorporates axial tension members which extend along the outside diameter of the inner tubular member over a substantial portion of the length of the catheter to a point proximal of the balloon. It is, however, recognized that the length of the axial tensioning members can be varied with resultant changes in the relative amount of force transferred from the proximal end of the catheter to the distal tip during oscillation.

The axial tensioning members are preferably wires or any other cord-like members which have a proximal end affixed to the outside diameter of the inner tubular member at a point proximate the manifold of the catheter, and a distal end affixed to the outside diameter of the inner tubular member at a point distal thereof. In preferred embodiments, the proximal and distal ends of the tensioning members both lie within the inflation lumen so that no seals are necessary where these elements would pass outside the lumen. The axial tensioning members are also preferably not affixed at any point intermediate between the proximal end and the distal end of each member. The axial tensioning members are manufactured from a material which is relatively inelastic when in tension relative to the elasticity of the inner tubular member when it is pulled in tension. Further, a plurality of axial tensioning members are preferably utilized and spaced equidistant about the circumference of the inner tubular member so that when the inner tubular member is pulled in a proximal direction, the axial tensioning members also pull the inner tubular member in an axial direction without deflecting any portion of the inner tubular member in a particular radial direction. This can be accomplished by including tensioning members equally spaced about the circumference of the inner tubular member or by always including opposing pairs or sets of axial tensioning members which are spaced at 180° relative to each other or equidistant around the circumference of the inner tubular member.

An advantage of the presently disclosed axial tensioning members is that they do not significantly impact the flexibility of the catheter over the length that the axial tensioning members extend. Because the tension members are not affixed at any point other than at their proximal and distal ends, the tubular members are free to bend with the axial tensioning members providing only a slight increase in stiffness. If the axial tensioning members were in fact affixed to the inner tubular member over their length, the inner tubular member would be stiffened over the entire length of the axial tensioning members to a significant degree. This alternative embodiment may be desired in certain applications. In an alternative embodiment, the axial tensioning members could be incorporated into the inner tubular member as an embedded braid or helical coil, which extends from near the proximal end to a point substantially distal. The inner member could also include a proximal portion which incorporates a braid, making it relatively less elastic in tension, and a distal portion affixed to the proximal portion and extending distally with a coextensive lumen. The distal portion would preferably have no braid and be relatively elastic.

The present invention is best understood in terms of operation of the catheter when a tight blockage or curve is encountered. During insertion of the catheter, the balloon is in a deflated state and wrapped around the inner tubular member. The folded balloon provides column support in the balloon region so that the balloon does not accordion when the inner tubular member is moved in a proximal axial direction. Thus, during insertion, when a tight blockage is encountered, the physician can axially oscillate the inner tubular member by pulling proximally on the proximal end or portion of the inner tubular member. When pulling the inner tubular member in a proximal direction, the axial tensioning members become taut. With increased force on the inner in the proximal direction, the inner tubular member distal of the distal point of attachment of the tensioning members is stretched in tension, while the outer tubular member becomes increasingly compressed. Thus, energy is stored both in the portion of the inner tubular member distal of the distal point of attachment of the axial tensioning members and also throughout the outer tubular member. When the physician releases the tensioned inner tubular member, this stored energy is also released, and the distal tip is forced in a distal direction. Due to the axial tensioning members, the point of application of the force on the inner tubular member is as though a hand is grasping this tubular member at this distal point of attachment and pushing the inner tubular member forward. This provides dramatically increased force transfer to the distal tip and significantly improves the ability of the tip to cross a tight blockage. Repeated oscillations of the inner tubular member, in combination with continued attempts to advance the catheter, advances the entire unit forward through the tight blockage.

When the tight blockage is crossed and the balloon is in its proper position within the blockage, the means for securing and/or sealing the inner tubular member is activated so that the balloon may be inflated without leakage of inflation fluid or movement of the inner relative to the outer in response to increased balloon pressure.

To facilitate repeated oscillation of the distal tip of the catheter via the oscillation of the inner tubular member as described above, the present invention further includes a detachable assembly which can be mounted to the proximal end of the manifold of the catheter. The detachable assembly includes both a valve assembly and an actuator assembly. The valve assembly includes a housing which has a valve activation mechanism rotatably disposed therein. By rotation of this mechanism, the valve can be tightened to a sealing position and loosened to a non-sealing position, wherein the inner tubular member is free to slide in an axial direction. The actuator assembly includes means for releasably attaching the distal end of the actuator assembly to the proximal end of the inner tubular member. The actuator assembly includes a spring-loaded piston mechanism which may be moved over a predetermined distance in the axial direction. Thus, the piston assembly is moved in a proximal direction to tension the inner tubular member and released to release the stored energy from such tensioning. In preferred embodiments, a spring means is included in the piston assembly so that as the piston assembly is moved proximally, the spring assembly is compressed so that when the piston is released the spring provides additional force in the distal direction as the energy stored in the catheter is released.

In one alternative embodiment of the present invention, the axial tensioning members of the present invention are incorporated into a single operator exchange catheter. With this embodiment, the inner tubular member extends over a distal portion of the catheter assembly with a proximal guide wire entry port located a substantial distance from the proximal end of the catheter. Axial tensioning members extend proximally from the point of attachment on the outside surface of the inner tubular member to the proximal end of the catheter shaft where they may extend through a seal assembly to the outside of the manifold, or alternatively, may be attached to a short stylet which in turn passes through a seal assembly for oscillating the catheter tip. A single operator exchange embodiment functions in the same way as the over-the-wire embodiment described above.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples provided have suitable alternatives which may also be utilized.

Figure 1:
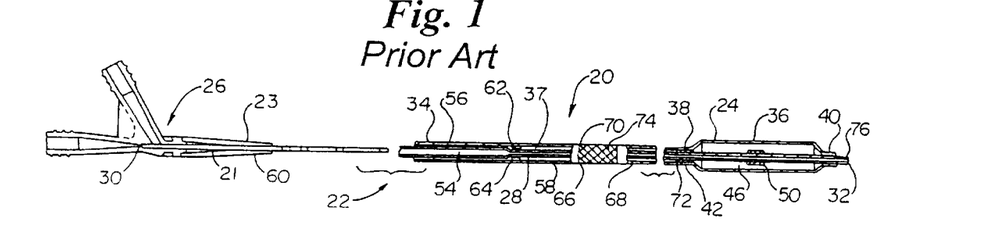
FIG. 1 is a cross-sectional view of a catheter showing a standard over-the-wire catheter.

Referring now to the drawings, FIG. 1 is a cross-sectional view of a standard over-the-wire balloon catheter. Such balloon catheter is disclosed in commonly assigned pending application Ser. No. 08/950,864, filed Oct. 15, 1997, entitled "Over-the-Wire Catheter with Improved Trackability", the disclosure of which is incorporated herein by reference.

The balloon catheter 20 includes a shaft assembly 22 and a balloon assembly 24 connected proximate its distal end. A conventional OTW-type manifold assembly 26 is connected to the proximal end of the shaft assembly 22. The shaft assembly 22 includes an inner tube 28 having a proximal end 30 and a distal end 32. The proximal end of the shaft assembly 21 extends into the manifold assembly 26, adhesively bonded to the shaft assembly 22. A polyurethane strain relief 23 is snap-fit to the manifold assembly 26, and the shaft assembly 22 extends into the manifold assembly 26 through the polyurethane strain relief 23. An outer tube 34 is coaxially disposed about the inner tube 28 to define an annular inflation lumen 37.

The balloon assembly 24 includes a balloon body portion 36 with a proximal balloon waist 38 and a distal balloon waist 40. The proximal balloon waist 38 is connected to the outer tube near its distal end 42 by means of an adhesive. The distal balloon waist 40 is connected to the inner tube 28 near its distal end 32 by means of an adhesive bond such that the interior of the balloon 46 is in fluid communication with the annular inflation lumen 37.

A radiopaque marker band 50 is preferably adhesively secured with cyanoacrylate to the inner tube 28 at a point underneath the balloon body 36. Alternatively, the marker band may be swaged onto the outer surface of the inner tube 28. The inner tube 28 defines a guide wire lumen 54 which provides a passage for a guide wire (not shown). The outer tube 34 defines an annular inflation lumen 37 which is in fluid communication with the interior of the balloon 46.

As previously stated, the catheter of the present invention preferably includes an outer tube having a relatively stiff proximal outer section, a midshaft section of lesser stiffness, and a tapering distal outer section of the least stiffniess. The progressive arrangement of more flexible materials as the catheter proceeds distally provides an optimal level of pushability and trackability to navigate tortuous vasculature.

The outer tube 34 has a relatively stiff, proximal outer section 56 with a proximal end 60 and a distal end 62. The proximal outer tube may be made of nylon, a polyamide, such as DURETHAN available from Bayer, a DURETHAN braid or polyetheretherketone (PEEK) braid. A preferred embodiment of PEEK braid is a variable PIC tube, wherein the PIC varies from about 30 to 100 PIC to give varying flexibility over the length of the proximal outer tube. The PIC preferably varies from about 50 to about 80. The braiding material in the PEEK or DURETHAN (polymer) braid may be made from stainless steel, or Nitinol (nickel titanium alloy). The proximal outer section 56 will preferably have an outside diameter ranging from 0.040 inches to 0.045 inches with a wall thickness ranging from 0.0028 inches to 0.0044 inches.

A midshaft section 58 with a proximal end 64 and a distal end 66 extends distally from the distal end of the proximal outer section 62. The midshaft section 58 has a stiffniess less than that of the proximal outer section 56. The midshaft section 58 is preferably made from a polyamide, such as CRISTAMID available from Elf Atochem, having a durometer of about 81D. This midshaft section 58 will preferably have an outside diameter ranging from 0.040 inches to 0.045 inches with a wall thickness ranging from 0.0028 inches to 0.0044 inches.

The distal end of the proximal outer section 62 is preferably joined to the proximal end of the midshaft section 64 with a urethane adhesive bond or a thermal weld. A distal outer section 68 having a proximal end 70 and a distal end 72 extends distally from the distal end of the midshaft section 66 to the distal end of the outer tube 42. This distal outer section 68 is more flexible or has less stiffness than both the proximal outer section 56 and the midshaft section 58. The outer diameter of the distal outer section 68 will preferably taper from about 0.045 inches at the proximal end 70 to 0.030 inches at the distal end 72. This distal outer section 68 is preferably made of polyether block amide (PEBAX) with a durometer of 70D. Thus, the distal end of the distal outer section 72 will exhibit less stiffness than the proximal end of the distal outer section 70. The distal end of the midshaft section 66 is joined to the proximal end of the distal outer section 70 with a urethane adhesive bond or a thermal weld.

A Nitinol braid insert 74 with a length of about 1.0" is placed within the proximal end of the distal outer section 70 to provide strain relief and reduce kinkability at the midshaft/distal outer section junction. This Nitinol braid 74 has a 0.001"×0.005" ribbon.

The inner tube 28 is made of polyethylene such as MARLEX HDPE. At the proximal end of the inner tube 30, the inner tube 28 has an outside diameter ranging from 0.024 inches to 0.026 inches and preferably about 0.025 inches, with the inner tube 28 having an inside diameter ranging from 0.018 inches to 0.0195 inches for a 0.014 inch guide wire for which this lumen is designed to be compatible with. The inner tube 28 has a wall thickness ranging from 0.0026 inches to 0.004 inches and preferably about 0.0032 inches. The outside diameter to wall thickness ratio must be sufficiently small to minimize the propensity of kinking.

As the inner tube 28 extends distally through the junction area between the distal end of the proximal outer section 62 and the proximal end of the midshaft section 64 of the outer tube 28, both the inner and outer diameters of the inner tube 28 will taper from wider diameters to narrower diameters. Likewise, at the distal end of the inner tube 32, both the inner and outer diameters of the inner tube 28 will once again taper from wider diameters to narrower diameters as the tube extends distally.

In preferred embodiments, a distal tip 76 is formed on the distal end of the inner tube 32 where the inner tube 28 distally tapers from a larger outer diameter to a smaller outer diameter. The distal tip 76 may be simply a continuation of the inner tube beyond the distal end of the balloon, or alternatively, a separate tip member extending distally from a bond under the distal waist of the balloon.

The proximal catheter shaft portion is preferably about 35 to 45 inches in length with a preferred length of 42 inches.

The midshaft section is preferably about 1 to about 3 inches in length with a preferred length of 2 inches. The distal outer section having the most flexibility is preferably about 8 to about 12 inches in length with a preferred length of about 10 inches.

Figure 2:
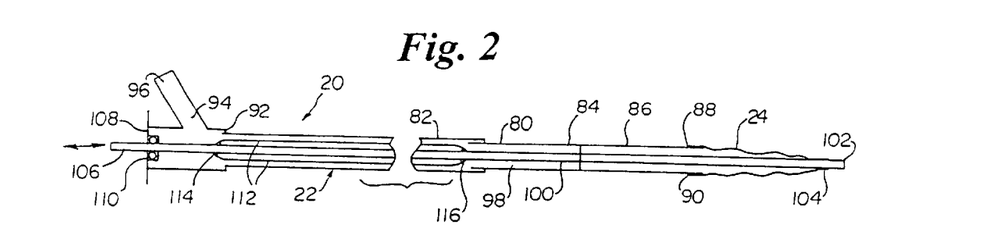
FIG. 2 is a schematic diagram of the catheter of FIG. 1 as modified to incorporate structure for axially oscillating the inner tubular member of the catheter.

Now referring to FIG. 2, a schematic representation of the catheter of the present invention is depicted. In particular, this figure focuses on those features which are incorporated into a catheter design of the present invention which allow for the oscillation of the inner tubular member relative to the outer tubular member and incorporates means for transmitting the force from the proximal end of the catheter to the distal tip for crossing a tight blockage within a vessel lumen. These features should be viewed in conjunction with an understanding of the catheter disclosed in FIG. 1, which is readily modified to incorporate such features.

As with the standard OTW catheter of FIG. 1, the catheter 20 of FIG. 2 includes a shaft assembly 22 and a balloon assembly 24. The balloon assembly 24 in the catheter of FIG. 2 is shown in a deflated state, as it would be when it is inserted within a vessel lumen. In its deflated state, the balloon member 24 is typically wrapped about the inner tubular member in tight fashion. As the inner tubular member is oscillated during insertion, the wrapped balloon provides column support so that the balloon member does not accordion or compress during such tensioning. The catheter 20 of FIG. 2 includes an outer tubular member 80 which preferably includes three sections, a proximal section 82, a midshaft section 84, and a distal outer shaft section 86, much like the catheter depicted in FIG. 1. The proximal waist 88 of the balloon is adhesively attached proximate the distal end 90 of the outer tubular member 80. The proximal end 92 of the outer tubular member 80 terminates in an adhesive bond within a manifold assembly 94 having a side port 96 in fluid communication with the internal lumen or inflation lumen 98 of the outer tubular member 80.

The inner tubular member 100 of the catheter 20 in FIG. 2 is slidably disposed through a lumen in the manifold 94 which is in axial alignment with the inner tubular member 100 as coaxially received within the outer tubular member 80. The inner tubular member 100 extends to the distal end of the catheter and preferably forms a tip 102 at its distal end. The distal waist of the balloon 104 is adhesively bonded proximate the distal end of the inner tubular member 100.

As previously stated, the inner tubular member has a proximal portion 106 which is slidably disposed within a lumen of the manifold 94. With this arrangement, as can be seen in FIG. 2, the inner tubular member proximal portion extends proximally outside the proximal end 108 of the manifold and can be moved in an axial direction, both proximally and distally. However, because the inflation lumen of the catheter 20 is formed in the annular space between the inner tubular member 100 and outer tubular member 80, inflation fluid would leak out the proximal end of the manifold absent a seal assembly 110 placed at a point proximal to the proximal end 92 of the outer tubular member. FIG. 2 shows schematically the seal assembly as including an O-ring type seal. Other types of seals could be utilized as would be chosen by one of skill in the art. In preferred embodiments, the seal assembly 110 is an active seal which can be alternated between an activated position, wherein the seal prevents leakage of inflation fluid and secures the inner tubular member in fixed axial relation to the outer tubular member and an inactive position which allows the inner tubular member to freely slide axially. The details of this type of seal are described in more detail with respect to the description below regarding FIG. 4.

As is also readily apparent from the schematic diagram of FIG. 2, if the proximal portion 106 of the inner tubular member 100 is oscillated in an axial direction, the distal tip 102 should also oscillate. However, it has been found that because the inner tubular member is relatively long and flexible, oscillating of the inner tubular member 100 at its proximal end 106 transfers very little force and oscillation to the distal tip 102 as the length of the inner tubular member is somewhat elastic and also tends to flex and bend when it is compressed or pushed forward. This problem is overcome by the incorporation of tensioning members 112 along a substantial portion of the length of the inner tubular member 100. A plurality of tensioning members 112 is preferably included so that as the proximal portion 106 of the inner tubular member 100 is pulled proximally, these tensioning members tighten and also pull in an axial direction without deflecting or bending the inner tubular member in a particular radial direction.

As depicted in FIG. 2, the tensioning members 112 preferably include a plurality of longitudinally extending or axially extending wires, wire-like members, or cords. In preferred embodiments, each of the tensioning members are affixed at a proximal end 114 to the outside wall of the inner tubular member 100 and the distal end 116 of the tensioning members are affixed to the outside diameter of the inner tubular member 100 at a point substantially distal from the proximal end of the catheter. Both the proximal end and the distal end of the tensioning members 112 are preferably located within the inflation lumen 98 or space between the inner and outer tubular member so that they do not penetrate to the outside of the catheter at any location which would require any type of seal assembly to prevent leakage of inflation fluid. Therefore, they are thus completely contained within the inflation lumen. In a preferred embodiment, the tensioning members 112 extend from a point proximate the manifold 94 to a point proximate the midshaft region of the catheter.

Further, the tensioning members 112 are preferably not affixed to the outside diameter of the inner tubular member 100 except at a location near their proximal end and their distal end. Because the tensioning members 112 are loose along a substantial portion of their length relative to the inner tubular member, the tensioning members do not affect the flexibility of the catheter in the regions through which they extend to any substantial degree. In an alternative embodiment, the tensioning members 112 could be embedded or attached over a substantial portion of their length if it is desired to stiffen that portion of the catheter shaft to a substantial degree. Alternatively, the tensioning members 112 could be affixed over selected portions of their length to provide further stiffening in those particular regions of the catheter.

A preferred embodiment includes tensioning members 112 which are simply metallic wires which are relatively inelastic in tension relative to the material of the inner tubular member 100. The key to functioning of the tensioning members to transfer force to the distal tip 102 of the catheter is the fact that the tensioning members are far less elastic than the inner tubular member when in tension. It is therefore understood that the tension members 112 could be replaced by a sleeve over the outside diameter of the inner tubular member which also is affixed at points proximate its proximal end and distal end so that it would function in the same manner as the wires previously disclosed. The material of the sheath would be required to be less elastic than the material of the inner tubular member 100 when in tension. Further, it is also understood that any number of tensioning members 112 could be utilized, with the key to their proper function being that the wires be evenly spaced about the outside circumference of the inner tubular member or be positioned in pairs or groupings which are equidistant around the circumference so that whatever number are chosen results in axial movement of the inner tubular member without substantial deflection or bending of the inner tubular member.

Figures 6, 7:
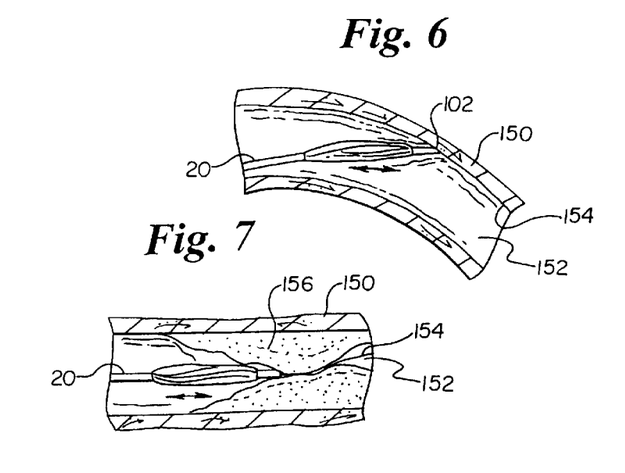
FIG. 6 is a schematic representation of problems encountered when it is necessary for a catheter distal tip to navigate a vessel bend which may include a stent mounted within such bend.
FIG. 7 is a schematic representation of a tight blockage within the vessel lumen through which a guide wire has been placed, but does not have adequate clearance for passage of the catheter.

The operation of the catheter of FIG. 2, to assist in crossing vessel restrictions or in navigating around the bend in a vessel, which may include a stent placed therein, is best understood in conjunction with a review of FIG. 6 and FIG. 7. Both FIGS. 6 and 7 depict a blood vessel 150 having a lumen 152 therethrough. The vessel of FIG. 6 depicts a bend in the vessel into which a catheter 20 extends. The device and vessel are not shown to scale, but rather shown to depict the principal operation of the present invention. The embodiment of FIG. 6 shows a guide wire 154 extending from the distal end 102 of the catheter. As shown, a problem which can occur when going around the bend in the vessel, is that the distalmost edge of the tip 102 catches on the vessel wall which may not be smooth, or if a stent (not shown) is implanted within the bend the leading edge may get caught on the struts of the stent. The catheter of FIG. 6 is shown oscillating, with movement of the tip shown in phantom. By oscillating the tip as it is moved forward it can readily be seen that such may be pulsed around the bend as the guide wire 154 is tracked.

In contrast to the depiction in FIG. 6, the depiction in FIG. 7 includes a restriction or blockage 156 within the vessel lumen 152. As depicted, a guide wire 154 has been navigated through the obstruction, but as is evident from the drawing, it would be difficult to pass the catheter 20 through such obstruction. Again, as is evident from the phantom view in FIG. 7, a pulsing of the distal tip of the catheter with sufficient force would assist in pushing the catheter through the obstruction.

Thus, in a situation as depicted in either FIGS. 6 or 7, the catheter of FIG. 2 is being inserted within the vessel lumen and reaches a point at which it is difficult to further advance the catheter. In such situation, the physician may then oscillate the proximal portion 106 of the inner tubular member 100 in an attempt to advance the catheter further. In doing such procedure, the physician would move the proximal portion 106 of the inner tubular member 100 in a proximal direction. By moving the inner tubular member 100 in a proximal direction, the inner tubular member is tensioned and essentially stretched to some degree. However, over the length of the inner tubular member 100, which includes the tensioning members 112, there would be little or no stretching. Therefore, as the inner tubular member is pulled proximally with increasing force, that portion of the inner tubular member 100 distal of the distal termination 116 of the tensioning members 112 stretches and stores energy.

Further, as the force pulling the inner tubular member 100 proximally is increased, the outer tubular member stores further energy by compression of the member to a degree relative to the force being applied. Once sufficient energy is stored, the proximal portion of the inner tubular member is released with the result that such stored energy in both the distal portion of the inner tubular member and the outer tubular member is released and causes the distal tip 102 to pulse forward with added force. Because the axial tensioning members 112 extend over a substantial portion of the length of the inner tubular member, the result is that the force is applied to the shaft and to the distal tip as though someone has grasped the inner tubular member 100 at the distal termination point 116 of the tensioning members, and pushed it forward. As is well recognized, the force transferred to the distal end of a tubular member increases as that force is applied nearer and nearer the distal end of that tubular member because the opportunity for bending or buckling of the tubular member is reduced. In this way, improved axial force is applied to the tip to aid in crossing a tight blockage or in navigating a tight bend which may include a blockage or a stent placed therein.

Figure 3:
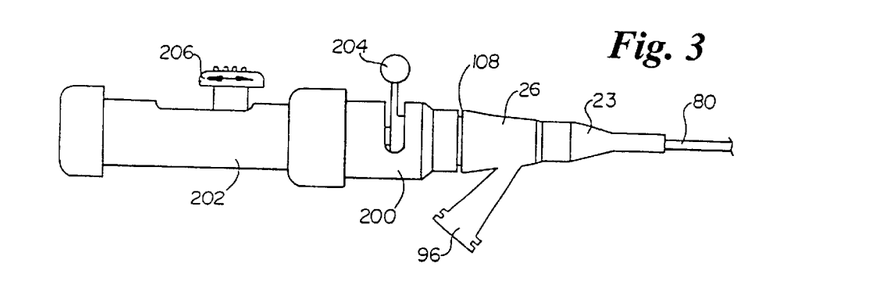
FIG. 3 is a plan view of a detachable assembly mounted to the proximal manifold of the catheter of FIG. 2 to provide an actuator assembly and valve assembly.
Figure 4:
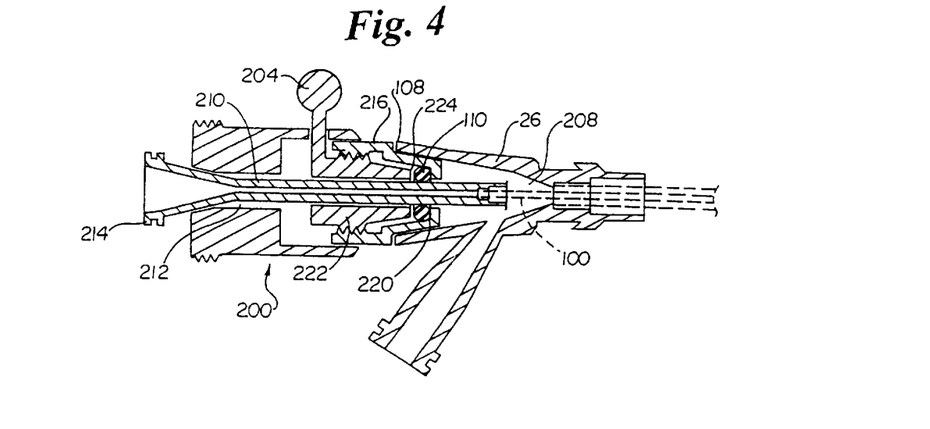
FIG. 4 is a cross-sectional view of the valve assembly of FIG. 3 as mounted on the proximal manifold of the catheter.
Figure 5:
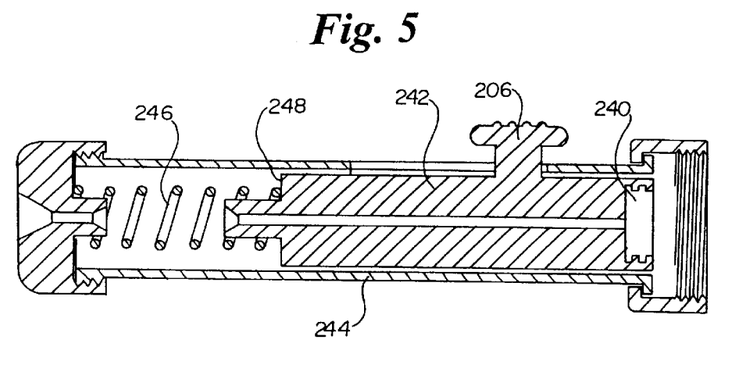
FIG. 5 is a cross-sectional view of the actuator assembly of FIG. 3 which can be threadably secured to the proximal end of the valve assembly.

FIGS. 3, 4 and 5 depict auxiliary equipment which can be utilized to facilitate the oscillation of the inner tubular member 100 within the catheter 20 of FIG. 2. FIG. 3 is a plan view which depicts a valve assembly 200 and an actuator assembly 202 which are releasably secured to the proximal end 108 of the manifold 26. This connection can include a luer type fitting or other releasable connection. The valve assembly 200 includes a valve handle 204, which may be moved from a first activated position to a second inactive position by rotation of the valve handle 204. The actuator assembly 202 includes a handle 206 which may be moved in an axial direction to oscillate the inner tubular member 100.

Referring now to FIG. 4, the valve assembly 200 is depicted in cross-sectional view for a better understanding of its operation. As depicted in FIG. 4, the inner tubular member 100 extends proximally into a chamber 208 within the manifold. An extension stem 210 is releasably secured to the proximal end of the inner tubular member with the stem extending proximally through the lumen 212 of the valve assembly 200. The stem assembly has a proximal end 214 which will be described in relationship to FIG. 5.

As seen in FIG. 4, the functioning portion of the seal assembly 200 includes a body 216 having a compressible member 110 or O-ring 110 deposited in abutting relationship with a stop member 220. The extension stem 210 passes through the O-ring. An activation member 222 is threadably received within the body 216 and has a forward compression face 224 which contacts and compresses the O-ring 110 when the valve handle 204 is rotated. In this way, the O-ring is compressed into sealing engagement with the outside diameter of the extension stem 210. This provides a seal and can assist in fixing the axial position of the inner tubular member 100 when the balloon is inflated. In an uncompressed state, the opening in the O-ring 110 allows for easy movement of the extension stem and inner tubular member 100 so that the member may be pulsed in an axial direction. It is recognized that the inner tubular member 100 could be extended further proximally so that the length of the extension stem may be significantly shortened or eliminated altogether should it be desired. Thus, the O-ring could simply engage the outside diameter of the inner tubular member 100 as it extends therethrough.

Next referring to FIG. 5, the actuator assembly 202 is depicted in cross-sectional view. With respect to FIG. 4, it was stated that the stem extension 210 terminates in a proximal end 214. In use, the proximal end 214 of the extension stem 210 is releasably secured to a distal end 240 of a piston member 242. The piston member 242 is integral with or attached to the handle 206 of the actuator assembly. The piston 242 is located within a housing 244 which guides the piston along an axial path. In preferred embodiments, a spring member 246 is disposed along the proximal end 248 of the piston member 242. In use, the piston is moved in a proximal direction so that the inner tubular member, as joined to the extension stem, are put in tension to store energy as described above. A spring member 246 is compressed as this movement in the proximal direction continues. The physician then can release the handle 206 to allow release of the energy stored in the catheter and in the spring to push the distal tip forward. With the actuator assembly, the physician can pulse the distal tip at a rapid rate as the catheter is moved forward. It is recognized that although a mechanical hand-operated actuator is depicted in FIG. 5, the operation could be motorized by simply attaching a motor and associated assemblies for reciprocating the piston, as would be well known in the art.

Figure 8:
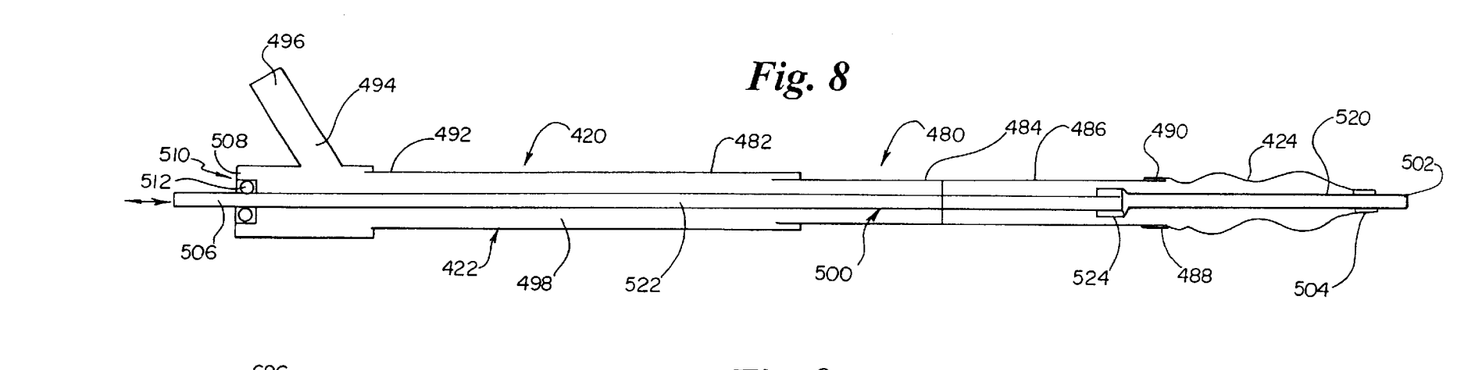
FIG. 8 is a schematic diagram of an alternative embodiment of the catheter of FIG. 1 incorporating an embedded braid in a proximal inner shaft.

Now referring to FIG. 8, a schematic representation of an additional embodiment of the present invention is depicted. In particular, this embodiment incorporates an inner tubular member having a proximal portion with an embedded braid. The embedded braid renders the proximal portion relatively inelastic in tension, as the previously disclosed axial tensioning members. However, the embedded braid also affect the flexibility of the proximal portion, which may be desirable in select applications. The inner tubular member of this embodiment also includes a distal portion which is relatively elastic, preferably including a tubular member free of embedded braid. The proximal and distal portions can be formed of a single tubular member or include separate segments bonded to form a coextensive lumen.

Catheter 420 of FIG. 8 includes a shaft assembly 422 and a balloon assembly 424. Balloon assembly 424 of catheter 420 is shown in a deflated state, as it would be when it is inserted within a vessel lumen. In its deflated state, balloon member 424 is typically wrapped about an inner tubular member 500 in tight fashion. As inner tubular member 500 is oscillated during insertion, the wrapped balloon provides column support so that the balloon member does not accordion or compress substantially during such tensioning. As with the previous embodiment, catheter 420 of FIG. 8 includes an outer tubular member 480 which preferably includes three sections, a proximal section 482, a midshaft section 484, and a distal outer shaft section 486.

A proximal waist 488 of balloon assembly 424 is adhesively attached proximate a distal end 490 of outer tubular member 480. Proximal end 492 of outer tubular member 480 terminates in an adhesive bond within a manifold assembly 494 having a side port 496 in fluid communication with an internal inflation lumen 498 of outer tubular member 480.

Inner tubular member 500 of catheter 420 is slidably disposed through a lumen in manifold 494 which is in axial alignment with inner tubular member 500 as coaxially received within outer tubular member 480. Inner tubular member 500 extends to the distal end of the catheter and preferably forms a tip 502 at its distal end. The distal waist of the balloon 504 is adhesively bonded proximate the distal end of inner tubular member 500.

In the present embodiment, inner tubular member 500 has a proximal portion 506 which is slidably disposed within a lumen of manifold 494. With this arrangement, as can be seen in FIG. 8, a proximal end 506 of inner tubular member 500 extends proximally outside a proximal end 508 of manifold 494. Proximal end 506 of inner tubular member 500 can be moved in an axial direction, both proximally and distally.

FIG. 8 shows schematically a sliding seal assembly 510 including an O-ring 512. Other types of seals could be utilized as would be chosen by one of skill in the art. In preferred embodiments, the seal assembly 510 is an active seal which can be alternated between an activated position, wherein the seal prevents leakage of inflation fluid and secures the inner tubular member in fixed axial relation to the outer tubular member, and an inactive position, which allows the inner tubular member to freely slide axially.

As is readily apparent from the schematic diagram of FIG. 8, if the proximal portion 506 of the inner tubular member 500 is oscillated in an axial direction, the distal tip 502 should also oscillate. Inner tubular member 500 is comprised of a distal portion 520 and a proximal portion 522. The proximal end of distal portion 520 is connected to the distal end of proximal portion 522 at a joint 524. Those with skill in the art will readily recognize that a number of methods may be used to join distal portion 520 to proximal portion 522. Methods which have been found acceptable include thermal welding, and joining with an adhesive in a lap joint configuration.

Distal portion 520 of inner tubular member 500 is preferably comprised of polyethylene, such as MARLEX HDPE. Proximal portion 522 of inner tubular member 500 is comprised of a material which is substantially less elastic than the material comprising outer tubular member 480. In a preferred embodiment, proximal portion 522 of inner tubular member 500 is comprised of a spring temper stainless steel braid encapsulated in polyimide. It is also preferred that a low friction layer 526 (not shown) be disposed on the inner diameter of proximal portion 522 of inner tubular member 500. A preferred material for low friction layer 526 is polytetrafluoroethylene (PTFE).

As described above, proximal portion 522 of inner tubular member 500 is relatively inelastic along its longitudinal axis relative to the material of outer tubular member 422. The relative longitudinal stiffniess of proximal portion 522 aids in oscillating tip 502 of catheter 420. Oscillating tip 502 is desirable when it is necessary to pass catheter tip 502 through a tight blockage or navigate catheter tip 502 through a tight bend. The desired oscillations may be generated by pulling in a proximal direction on proximal end 506 of proximal portion 522, or by pushing in a distal direction on proximal end 506 of proximal portion 522.

When proximal portion 522 is pulled proximally with increasing force, distal portion 520 stretches and stores energy. Likewise, balloon assembly 424, which is wrapped tightly as described above, and outer tubular member 422 store further energy by compression. Once sufficient energy is stored, proximal end 506 is released with the result that such stored energy in catheter 420 is released and causes distal tip 502 to pulse forward.

The present invention has been described applied to an over-the-wire (OTW) catheter design. It is, however, recognized that the present design can be incorporated in a single operator exchange (SOE) catheter. With an SOE design, tensioning members can extend proximally from a distal point of attachment on a shortened distal guide wire tube. The tensioning members would extend proximally out of the proximal end of the manifold with a seal assembly operating to prevent leakage around the tensioning members. The distal tip can then be oscillated by axial movement of the tensioning wires by the operator to store energy in the shortened distal tube and outer shaft. Pulling the tensioning wires proximally with subsequent release of stored energy would cause the catheter to function in the same manner as the previous embodiment.

Figure 9:
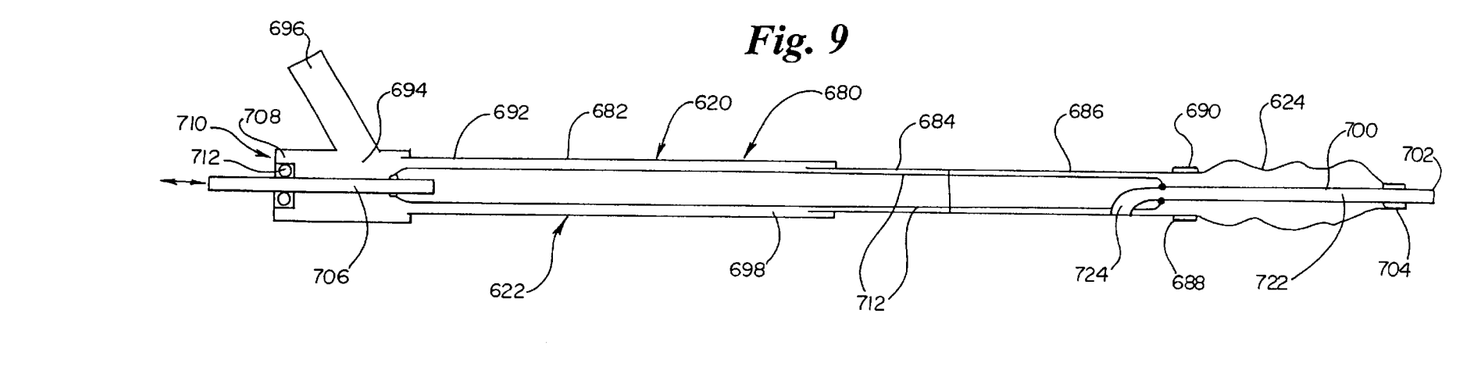
FIG. 9 is a schematic diagram of an alternative embodiment of the catheter of FIG. 1 depicting axial tensioning members incorporated in a single operator exchange catheter.

Now referring to FIG. 9, a schematic representation of a single operator exchange embodiment of the present invention is depicted. FIG. 9 is a plan view of a single-operator-exchange (SOE) catheter 620 including a shaft assembly 622 and a balloon assembly 624. Shaft assembly 622 includes an outer tubular member 680 which preferably includes three sections, a proximal section 682, a midshaft section 684, and a distal outer shaft section 686. Shaft assembly 622 also includes a distal inner tubular member 700 and a proximal inner tubular member 706.

The balloon assembly 624 in the catheter of FIG. 9 is shown in a deflated state, as it would be when it is inserted within a vessel lumen. In its deflated state, balloon member 624 is typically wrapped about distal inner tubular member 700 in tight fashion. As distal inner tubular member 700 is oscillated during insertion, the wrapped balloon provides column support so that the balloon member does not accordion or compress substantially during such tensioning.

A proximal waist 688 of balloon assembly 624 is adhesively attached proximate a distal end 690 of outer tubular member 680. A proximal end 692 of outer tubular member 680 terminates in an adhesive bond within a manifold assembly 694 having a side port 696 in fluid communication with the internal lumen or inflation lumen 698 of the outer tubular member 680.

Distal inner tubular member 700 includes a guidewire lumen 722 which is much shorter than the overall catheter length to facilitate rapid exchange of catheter 620 over a guidewire. Catheter 620 includes a port 724. A guidewire may access guidewire lumen 722 at port 724 and extend through guidewire lumen 722 emerging from distal tip 702 of catheter 620. Distal inner tubular member 700 and proximal inner tubular member 706 are connected by a plurality of tensioning members 712 which are disposed inside internal lumen 698 of catheter 620. As proximal inner tubular member 706 is pulled in a proximal direction, these tensioning members tighten and pull proximally on distal inner tubular member 700.

As depicted in FIG. 9, the tensioning members 712 preferably include a plurality of longitudinally extending or axially extending wires, wire-like members, or cords. In preferred embodiments, each of the tensioning members are affixed to the outside wall of proximal inner tubular member 706 and the outside wall of distal inner tubular member 700. Both the proximal end and the distal end of tensioning members 712 are preferably located within the inflation lumen 698 so that they do not penetrate to the outside of the catheter at any location which would require any type of seal assembly to prevent leakage of inflation fluid. The seal assembly acts on proximal inner tubular member 706 in this embodiment. In an alternative embodiment, proximal inner tubular member 706 could be eliminated and tensioning members 712 could extend proximally through the seal assembly with the seal acting directly on the tensioning members 712.

In a preferred embodiment, the tensioning members 712 extend from a point proximate the manifold 694 to a point proximate distal section 686 of outer tubular member 680. Further, the tensioning members 712 are preferably not affixed to the inside diameter of outer tubular member 680. Because tensioning members 712 are loose along a substantial portion of their length relative to outer tubular member 680, distal inner tubular member 700, proximal inner tubular member 706, and tensioning members 712 do not affect the flexibility of catheter 620 in regions through which they extend to any substantial degree.

A preferred embodiment includes tensioning members 712 which are simply metallic wires which are relatively inelastic in tension relative to the material of outer tubular member 680. The ability of tensioning members 712 to transfer force to distal tip 702 of catheter 620 is due to the fact that tensioning members 712 are far less elastic than distal inner tubular member 700 and outer tubular member 680 when in tension.

It should be understood that any number of tensioning members 712 could be utilized and that tensioning members 712 need not be wires. For example, tensioning members 712 could be comprised of a single tube which is relatively rigid along its longitudinal axis, but relatively flexible perpendicular to its longitudinal axis.

When it is necessary for catheter tip 702 to cross a tight blockage or navigate a tight bend, a physician may cause tip 702 to oscillate. Oscillating tip 702 aids in stepping tip 702 through obstacles. The oscillations are generated by pulling in a proximal direction on proximal inner tubular member 706.

As proximal inner tubular member 706 is pulled proximally with increasing force, distal inner tubular member 700 is stretched and stores energy. Likewise, balloon assembly 624, which is wrapped tightly as described above, and outer tubular member 680 store further energy by compression. Once sufficient energy is stored, proximal inner tubular member 706 is released with the result that such stored energy in catheter 620 is released and causes distal tip 702 to pulse forward. Because tensioning members 712 extend over a substantial portion of the length of catheter 620, the result is that the force is applied to distal tip 702 as though someone had grasped the distal inner tubular member 700 and pushed it forward. As is well recognized, the force transferred to the distal end of a tubular member increases as that force is applied nearer and nearer the distal end of that tubular member because the opportunity for bending or buckling of the tubular member is reduced. In this way, improved axial force is applied to the tip to aid in crossing a tight blockage or in navigating a tight bend which may include a blockage or a stent placed therein.

Having thus described the preferred embodiments of the present invention, those of skill in the art will readily appreciate that yet other embodiments may be made and used within the scope of the claims hereto attached.

What is claimed:

1. A balloon catheter assembly for improved movement through severely obstructed or highly tortuous vessel lumens, said balloon catheter assembly comprising:

a. a manifold assembly having an outer tube extending distally therefrom and inner tube slidably disposed through a lumen of said manifold assembly in axial alignment with said outer tube, said inner tube having a proximal portion accessible for oscillating said inner tube in an axial direction within said lumen of said manifold assembly, said inner and outer tube extending distally from said manifold with said inner tube coaxially disposed within said outer tube to form an inflation lumen therebetween in fluid communication with a balloon affixed proximate a distal end of said inner and outer tubes; and, b. at least one axial tensioning member having a proximal portion affixed to said inner tube proximate said manifold assembly and a distal portion affixed to said inner tube distal of said manifold assembly.

2. The balloon catheter assembly of claim 1, wherein said axial tensioning member comprises a plurality of wire-like members.

3. The balloon catheter assembly of claim 2, wherein said plurality of wire-like members are less elastic in tension than said inner tube.

4. The balloon catheter assembly of claim 1, wherein said axial tensioning member is a tubular sheath disposed over said inner tube, said sheath less elastic in tension than said inner tube.

5. The balloon catheter assembly of claim 1, further comprising a seal assembly operatively disposed in relation to said inner tube and manifold assembly to prevent inflation fluid from leaking out of the proximal end of said manifold assembly around said inner tube outer surface as slidably disposed therein.

6. The balloon catheter assembly of claim 5, wherein said seal assembly includes means for engaging and disengaging said seal assembly so that when said seal is disengaged said inner tube is free to move axially.

7. The balloon catheter assembly of claim 5, further comprising a means for oscillating said inner tube in an axial direction, said means coupled to said proximal portion of said inner tube.

8. An over-the-wire type balloon catheter comprising:
   a. an outer tube affixed to a manifold assembly proximate a proximal end of said outer tube and having a proximal portion of an inflatable balloon assembly affixed proximate a distal end of said outer tube, wherein said outer tube has a lumen extending therethrough in fluid communication with an interior volume of said balloon at a distal end of said lumen and a proximal end of said lumen is in fluid communication with a lumen extending within said manifold assembly to a first manifold port;
   b. an inner tube coaxially disposed within said lumen of said outer tube to form an inflation lumen therebetween, said inner tube having a distal portion extending distally beyond said distal end of said outer tube and having a distal portion of said inflatable balloon assembly affixed proximate a distal end of said inner tube, said inner tube having a proximal portion slidably disposed within said lumen of said manifold assembly in axial alignment with said outer tube, wherein said proximal portion of said inner tube extends proximally to a second port in said manifold assembly so that at least a portion of said proximal portion of said inner tube is accessible for axially oscillating said inner tube; and,
   c. a plurality of axial tensioning members, each of said axial tensioning members having a proximal portion affixed to said inner tube proximate said manifold assembly and each of said tensioning members has a distal portion affixed to said inner tube at a point distal of said manifold assembly, wherein at least a portion of at least one axial tensioning member is located in said inflation lumen.

9. The balloon catheter of claim 8, wherein said axial tensioning member comprises a plurality of wire-like members.

10. The balloon catheter of claim 9, wherein said plurality of wire-like members are less elastic in tension than said inner tube.

11. The balloon catheter of claim 8, wherein said plurality of axial tensioning members are disposed equidistant about the circumference of said inner tube.

12. The balloon catheter of claim 8, wherein at least some of said plurality of axial tensioning members are affixed to said inner tube over at least a portion of their length, in addition to proximal and distal portions.

13. The balloon catheter of claim 8, further comprising a seal assembly operatively disposed in relation to said inner tube and manifold assembly to prevent inflation fluid from leaking out of the proximal end of said manifold assembly around said inner tube outer surface as slidably disposed therein.

14. The balloon catheter of claim 13, wherein said seal assembly includes means for engaging and disengaging said seal assembly so that when said seal is disengaged said inner tube is free to move axially.

15. In an over-the-wire type catheter having an outer tube affixed to a manifold, and inner tube coaxially disposed with a lumen of the outer tube to form an inflation lumen therebetween which is in fluid communication with a balloon, said balloon having a proximal portion affixed to said distal portion of said outer tube and a distal portion affixed to said distal portion of said inner tube, with said balloon extending axially therebetween, the improvement comprising:
   a. a proximal portion of said inner tube slidably disposed within a lumen of said manifold assembly axially aligned therewith; and,
   b. a plurality of axial tensioning members extending over a portion of the length of said inner tube from proximate said manifold assembly to a selected distal location on said inner tube, said axial tensioning members affixed to said inner tube, wherein at least a portion of at least one axial tensioning member is located in said inflation lumen.

16. The catheter of claim 15, wherein said axial tensioning member comprises a plurality of wire-like members.

17. The catheter of claim 16, wherein said plurality of wire-like members are less elastic in tension than said inner tube.

18. The catheter of claim 15, wherein said plurality of axial tensioning members are disposed equidistant about the circumference of said inner tube.

19. The catheter of claim 15, wherein at least some of said plurality of axial tensioning members are affixed to said inner tube over at least a portion of their length, in addition to proximal and distal portions.

20. The catheter of claim 15, further comprising a seal assembly operatively disposed in relation to said inner tube and manifold assembly to prevent inflation fluid from leaking out of the proximal end of said manifold assembly around said inner tube outer surface as slidably disposed therein.

21. A single operator exchange catheter comprising:
   a. an outer tube affixed to a manifold assembly proximate a proximal end of said outer tube and having a proximal portion of an inflatable balloon assembly affixed proximate a distal end of said outer tube, wherein said outer tube has a lumen extending therethrough in fluid communication with an interior volume of said balloon at a distal end of said lumen and a proximal end of said lumen is in fluid communication with a lumen extending within said manifold assembly to a first manifold port;
   b. a distal inner tube coaxially disposed within said lumen of said outer tube, said distal inner tube having a distal portion extending distally beyond said distal end of said outer tube and having a distal portion of said inflatable balloon assembly affixed proximate a distal end of said distal inner tube, said distal inner tube having a guidewire lumen;

c. a proximal inner tube coaxially disposed within said lumen of said outer tube, said proximal inner tube having a proximal portion slidably disposed within said lumen of said manifold assembly in axial alignment with said outer tube, wherein said proximal portion of said proximal inner tube extends proximally to a second port in said manifold assembly so that at least a portion of said proximal portion of said proximal inner tube is accessible for axially oscillating said proximal inner tube; and d. a plurality of axial tensioning members, each of said axial tensioning members having a proximal portion affixed to said proximal inner tube and each of said tensioning members has a distal portion affixed to said distal inner tube.

22. The balloon catheter of claim 21, wherein said plurality of axial tensioning members comprises a plurality of wire-like members.

23. The balloon catheter of claim 22, wherein said plurality of wire-like members are less elastic in tension than said inner tube.

* * * * *